United States Patent
Locke et al.

(10) Patent No.: US 11,813,393 B2
(45) Date of Patent: *Nov. 14, 2023

(54) COLLAPSIBLE CANISTER FOR USE WITH REDUCED PRESSURE THERAPY DEVICE

(71) Applicant: KCI Licensing, Inc., San Antonio, TX (US)

(72) Inventors: Christopher Brian Locke, Bournemouth (GB); Aidan Marcus Tout, Alderbury (GB)

(73) Assignee: KCI Licensing, Inc., San Antonio, TX (US)

(*) Notice: Subject to any disclaimer, the term of this patent is extended or adjusted under 35 U.S.C. 154(b) by 95 days.

This patent is subject to a terminal disclaimer.

(21) Appl. No.: 17/536,856

(22) Filed: Nov. 29, 2021

(65) Prior Publication Data

US 2022/0080104 A1    Mar. 17, 2022

Related U.S. Application Data

(63) Continuation of application No. 16/001,720, filed on Jun. 6, 2018, now Pat. No. 11,219,712, which is a continuation of application No. 14/162,285, filed on Jan. 23, 2014, now Pat. No. 10,016,542.

(60) Provisional application No. 61/780,056, filed on Mar. 13, 2013.

(51) Int. Cl.
*A61M 1/00* (2006.01)

(52) U.S. Cl.
CPC ............ *A61M 1/602* (2021.05); *A61M 1/882* (2021.05); *A61M 1/90* (2021.05); *A61M 1/98* (2021.05)

(58) Field of Classification Search
CPC . A61M 1/0088; A61M 1/0096; A61M 1/0015
See application file for complete search history.

(56) References Cited

U.S. PATENT DOCUMENTS

| | | | |
|---|---|---|---|
| 1,355,846 A | 10/1920 | Rannells | |
| 2,397,257 A * | 3/1946 | Goland | A61M 1/68 D24/111 |
| 2,547,758 A | 4/1951 | Keeling | |
| 2,632,443 A | 3/1953 | Lesher | |

(Continued)

FOREIGN PATENT DOCUMENTS

| AU | 550575 B2 | 3/1986 |
|---|---|---|
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Guy K Townsend (57) ABSTRACT

A wound fluid collection system includes a canister with a chamber fluidly connected to a wound dressing in a tissue site through an inlet and also fluidly connected to a reduced pressure source through an outlet. At least a portion of the canister is collapsible and yet can be maintained in an extended state when exposed to subatmospheric pressure. The canister is releasably attachable to a supporting member.

19 Claims, 3 Drawing Sheets

(56) References Cited

U.S. PATENT DOCUMENTS

| | | | |
|---|---|---|---|
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,084,691 A * | 4/1963 | Stoner | A61M 1/82 604/134 |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,742,952 A * | 7/1973 | Magers | A61M 1/684 604/133 |
| 3,774,611 A * | 11/1973 | Tussey | A61M 1/68 417/472 |
| 3,809,087 A * | 5/1974 | Lewis, Jr. | A61M 1/68 604/134 |
| 3,826,254 A | 7/1974 | Mellor | |
| 3,875,941 A * | 4/1975 | Adair | A61M 1/684 141/26 |
| 4,080,970 A | 3/1978 | Miller | |
| 4,096,853 A | 6/1978 | Weigand | |
| 4,098,434 A * | 7/1978 | Uhlig | B65D 83/0055 222/105 |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,278,089 A * | 7/1981 | Huck | A61M 1/684 417/328 |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,392,860 A * | 7/1983 | Huck | A61M 1/684 604/212 |
| 4,397,643 A * | 8/1983 | Rygiel | A61M 1/602 600/573 |
| 4,419,097 A | 12/1983 | Rowland | |
| 4,429,693 A * | 2/1984 | Blake | A61M 1/68 604/319 |
| 4,455,140 A * | 6/1984 | Joslin | A61M 1/602 D24/117 |
| 4,465,485 A | 8/1984 | Kashmer et al. | |
| 4,475,909 A | 10/1984 | Eisenberg | |
| 4,480,638 A | 11/1984 | Schmid | |
| 4,525,166 A * | 6/1985 | Leclerc | A61M 1/68 604/313 |
| 4,525,374 A | 6/1985 | Vaillancourt | |
| 4,529,402 A * | 7/1985 | Weilbacher | A61M 1/684 D24/111 |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,643,719 A * | 2/1987 | Garth | A61M 1/84 604/315 |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,950,247 A * | 8/1990 | Rosenblatt | A61M 1/784 600/580 |
| 4,953,565 A | 9/1990 | Tachibana et al. | |
| 4,969,880 A | 11/1990 | Zamierowski | |
| 4,981,473 A * | 1/1991 | Rosenblatt | A61M 1/684 600/573 |
| 4,985,019 A | 1/1991 | Michelson | |
| 5,019,059 A * | 5/1991 | Goldberg | A61M 1/684 604/317 |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,102,404 A * | 4/1992 | Goldberg | A61M 1/684 D24/117 |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,248,300 A * | 9/1993 | Bryant | A61M 5/14244 222/103 |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,374,257 A * | 12/1994 | Drainville | A61M 1/602 604/408 |
| 5,437,622 A | 8/1995 | Carion | |
| 5,437,651 A | 8/1995 | Todd et al. | |
| 5,451,218 A * | 9/1995 | Moore | A61F 5/4404 604/317 |
| 5,484,428 A * | 1/1996 | Drainville | A61M 1/60 604/408 |
| 5,505,717 A * | 4/1996 | Moore | A61F 5/4404 604/329 |
| 5,527,293 A | 6/1996 | Zamierowski | |
| 5,542,939 A * | 8/1996 | Onodera | A61M 1/67 417/469 |
| 5,549,584 A * | 8/1996 | Gross | A61M 1/915 604/319 |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,656,149 B2 * | 12/2003 | Ladd | A61M 1/602 604/316 |
| 6,814,079 B2 | 11/2004 | Heaton et al. | |
| 7,846,141 B2 | 12/2010 | Weston | |
| 8,007,257 B2 * | 8/2011 | Heaton | A61M 1/78 604/319 |
| 8,062,273 B2 | 11/2011 | Weston | |
| 8,216,198 B2 | 7/2012 | Heagle et al. | |

(56) References Cited

U.S. PATENT DOCUMENTS

| | | | |
|---|---|---|---|
| 8,251,979 B2* | 8/2012 | Malhi | A61M 1/882 604/9 |
| 8,257,327 B2 | 9/2012 | Blott et al. | |
| 8,398,614 B2 | 3/2013 | Blott et al. | |
| 8,414,519 B2* | 4/2013 | Hudspeth | A61M 1/742 604/313 |
| 8,449,509 B2 | 5/2013 | Weston | |
| 8,529,548 B2 | 9/2013 | Blott et al. | |
| 8,535,283 B2* | 9/2013 | Heaton | A61M 1/98 604/319 |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,641,692 B2* | 2/2014 | Tout | A61M 1/68 604/316 |
| 8,679,079 B2* | 3/2014 | Heaton | A61M 1/80 604/319 |
| 8,679,081 B2 | 3/2014 | Heagle et al. | |
| 8,834,451 B2 | 9/2014 | Blott et al. | |
| 8,834,452 B2* | 9/2014 | Hudspeth | A61M 1/742 604/313 |
| 8,864,748 B2* | 10/2014 | Coulthard | A61M 1/96 602/42 |
| 8,926,592 B2 | 1/2015 | Blott et al. | |
| 9,017,302 B2 | 4/2015 | Vitaris et al. | |
| 9,028,458 B2* | 5/2015 | Heaton | A61M 1/82 604/315 |
| 9,198,801 B2 | 12/2015 | Weston | |
| 9,211,365 B2 | 12/2015 | Weston | |
| 9,289,542 B2 | 3/2016 | Blott et al. | |
| 9,561,312 B2* | 2/2017 | Heaton | A61M 1/84 |
| 9,795,722 B2* | 10/2017 | Tout | A61M 1/732 |
| 9,925,312 B2* | 3/2018 | Heaton | A61M 1/82 |
| 10,016,542 B2* | 7/2018 | Locke | A61M 1/982 |
| 10,064,984 B2* | 9/2018 | Locke | A61M 1/96 |
| 10,092,682 B2* | 10/2018 | Locke | A61M 1/602 |
| 10,226,553 B2* | 3/2019 | Heaton | A61M 1/982 |
| 10,398,808 B2* | 9/2019 | Heaton | A61M 1/684 |
| 11,219,712 B2* | 1/2022 | Locke | A61M 1/602 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2008/0108977 A1* | 5/2008 | Heaton | A61M 1/78 604/355 |
| 2008/0200905 A1* | 8/2008 | Heaton | A61M 1/784 604/543 |
| 2009/0292263 A1* | 11/2009 | Hudspeth | A61M 1/984 604/313 |
| 2010/0030166 A1* | 2/2010 | Tout | A61M 1/684 604/316 |
| 2011/0295220 A1* | 12/2011 | Heaton | A61M 1/73 604/319 |
| 2013/0338614 A1* | 12/2013 | Heaton | A61M 1/784 604/319 |
| 2014/0121614 A1* | 5/2014 | Tout | A61M 1/98 604/319 |
| 2014/0155849 A1* | 6/2014 | Heaton | A61M 1/98 604/319 |
| 2014/0163491 A1 | 6/2014 | Schuessler et al. | |
| 2014/0188061 A1* | 7/2014 | Locke | A61M 1/98 604/321 |
| 2014/0276488 A1* | 9/2014 | Locke | A61M 1/98 604/319 |
| 2015/0080788 A1 | 3/2015 | Blott et al. | |
| 2015/0238665 A1* | 8/2015 | Heaton | A61M 1/784 604/543 |
| 2015/0246164 A1* | 9/2015 | Heaton | A61M 1/882 604/313 |
| 2018/0339088 A1* | 11/2018 | Locke | A61M 1/90 |
| 2019/0009010 A1* | 1/2019 | Locke | A61M 1/96 |
| 2022/0080104 A1* | 3/2022 | Locke | A61M 1/90 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

(56) References Cited

OTHER PUBLICATIONS

Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164.
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

\* cited by examiner

COLLAPSIBLE CANISTER FOR USE WITH REDUCED PRESSURE THERAPY DEVICE

RELATED APPLICATION

This application is a continuation of U.S. patent application Ser. No. 16/001,720, filed Jun. 6, 2018, which is a continuation of U.S. patent application Ser. No. 14/162,285, filed Jan. 23, 2014, now issued as U.S. Pat. No. 10,016,542, which claims the benefit, under 35 USC § 119(e), of the filing of U.S. Provisional Patent Application Ser. No. 61/780,056, entitled "COLLAPSIBLE CANISTER FOR USE WITH REDUCED PRESSURE THERAPY DEVICE," filed Mar. 13, 2013, which is incorporated herein by reference for all purposes.

TECHNICAL FIELD

The present invention relates generally to tissue treatment systems and in particular to systems and methods for collecting wound fluid.

BACKGROUND

Clinical studies and practice have shown that providing a reduced pressure in proximity to a compromised tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifold device. The porous pad contains cells or pores that are capable of distributing reduced pressure to the tissue and channeling fluids that are drawn from the tissue.

Wound fluids, also known as exudates, are generally collected in a canister for disposal or analysis. Wound fluid primarily consists of plasma in addition to red and white blood cells, platelets, bacteria, and a variety of proteinaceous material. Plasma consists primarily of saline. In clinical practice, it is desirable that canisters are sized large enough to obviate the need for frequent replacement even when used in the treatment of wounds generating a high volume of exudate. Conversely, it is also desirable that the canister is not so bulky that the canister consumes too much storage space or unnecessary resources for hazardous waste disposal of canisters filled with potentially infectious wound fluid. In the home healthcare environment, storage and disposal issues are more pronounced. Caregivers in the home environment must also supply a bodily with empty canisters and dispose of filled canisters, so minimizing this burden and potential accidents resulting from the disposal of filled containers is useful as well as more cost-effective.

BRIEF SUMMARY

In an illustrative embodiment, a bodily fluid collection canister intended for use with a reduced pressure treatment unit wherein the canister comprises a generally rigid support member with a proximal end and a distal end. The proximal end includes an inlet and an outlet. The inlet is adapted to receive bodily fluids from a tissue site and the outlet is adapted to receive reduced pressure from a reduced pressure treatment unit. The support member is releasably connectable to the reduced pressure treatment unit. The canister also comprises a container having walls wherein the walls define a chamber. The container comprises a proximal end that includes an inlet to receive bodily fluids from a tissue site and an outlet to receive reduced pressure from a reduced pressure therapy unit. The container comprises a closed distal end. The walls of the container have a collapsible portion that allows the container to be compressed or collapsed and stretched or expanded. The canister also comprises a retention device to couple the distal end of the container to the distal end of the support member, holding the container in an expanded state.

In another illustrative embodiment, a bodily fluid collection canister intended for use with a reduced pressure treatment unit, the canister comprising a support member whose body is essentially rigid, a proximal end and a distal end. The proximal end includes an inlet to receive fluid from a tissue site and an outlet configured to receive reduced pressure via a fluid coupling. The support member is configured to be releasably connectable to the reduced pressure treatment unit. The canister also comprises a container with walls, the walls defining a chamber within the container. The canister includes a proximal end and a distal end. The proximal end includes an opening to the chamber fluidly connected to the inlet and outlet of the support member. The distal end of the container is closed, closing the chamber. The walls of the container comprise a collapsible portion that allows the container to be compressed or collapsed and stretched or expanded. The container also comprises a fluidic device such as a bladder or a pneumatic pouch located within the container. The fluidic device is adapted to be charged or filled with a fluid, either gaseous or liquid, such that when charged, the container is essentially stretched or expanded until the fluidic device is discharged.

In still another embodiment, a method for collecting bodily fluid from a tissue site is provided. The method may include expanding a canister from one volume to a greater volume and affixing the canister to a carrier plate. The method may include expanding a canister from one volume to a greater volume and charging a fluidic device that is integral to the canister such that the charged fluidic device substantially maintains the expanded state of the canister. The method may further include applying a reduced pressure to the canister such that bodily fluid is collected from the tissue site.

DETAILED DESCRIPTION OF ILLUSTRATIVE EMBODIMENTS

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The term "reduced pressure" as used herein generally refers to a pressure less than the ambient pressure at a tissue site that is being subjected to treatment. In most cases, this reduced pressure will be less than the atmospheric pressure at which the bodily is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "tissue site" as used herein refers to a wound or defect located on or within any tissue, including but not limited to, bone tissue, adipose tissue, muscle tissue, neural tissue, dermal tissue, vascular tissue, connective tissue, cartilage, tendons, ligaments, or parenchymatous tissue. The term "tissue site" may further refer to areas of any tissue that are not necessarily wounded or defective, but are instead areas in which it is desired to add or promote the growth of additional tissue.

Figure 1:
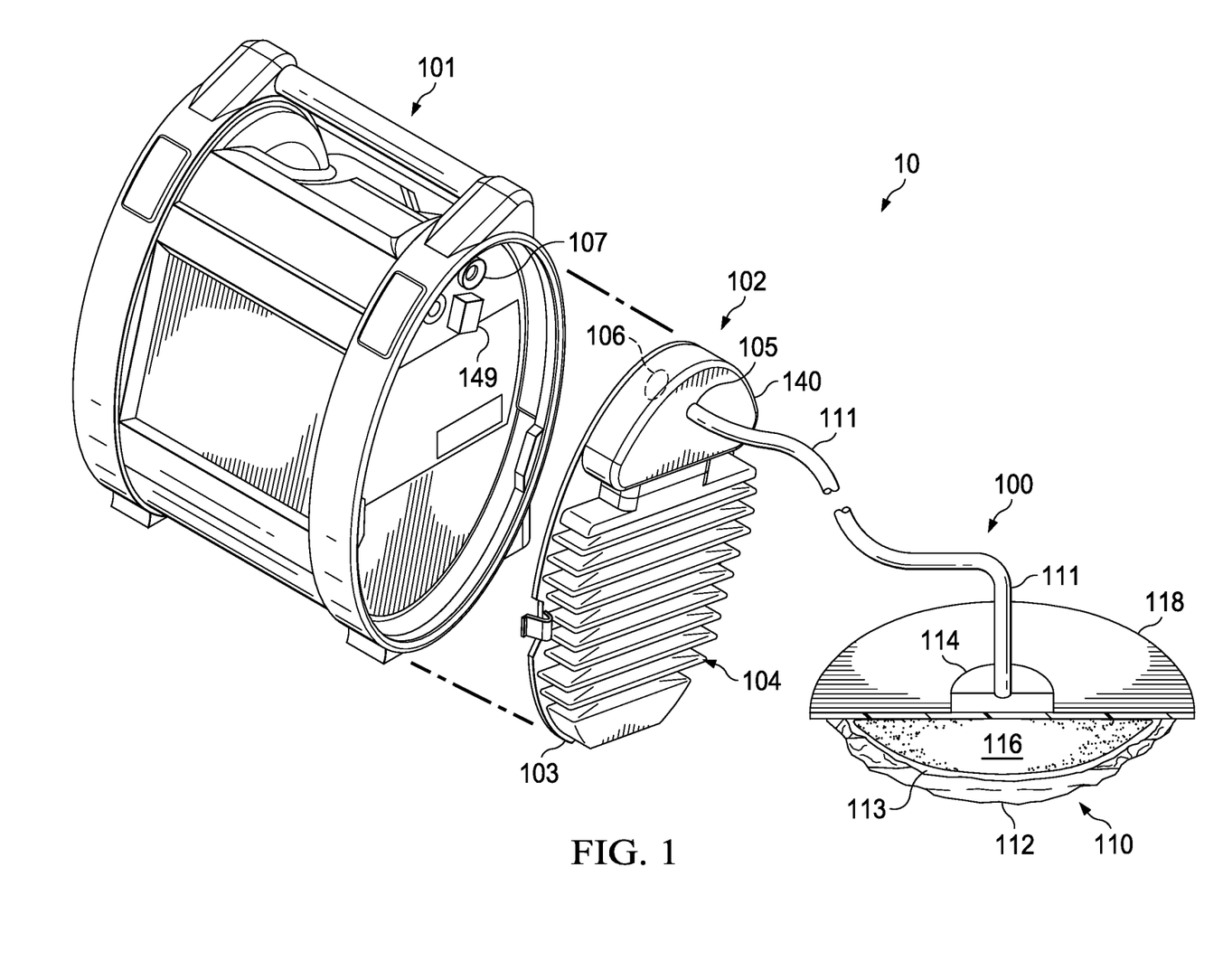
FIG. 1 depicts a perspective view of a reduced pressure treatment system having a fluid collection canister and a supporting member according to an illustrative embodiment.
Figure 2:
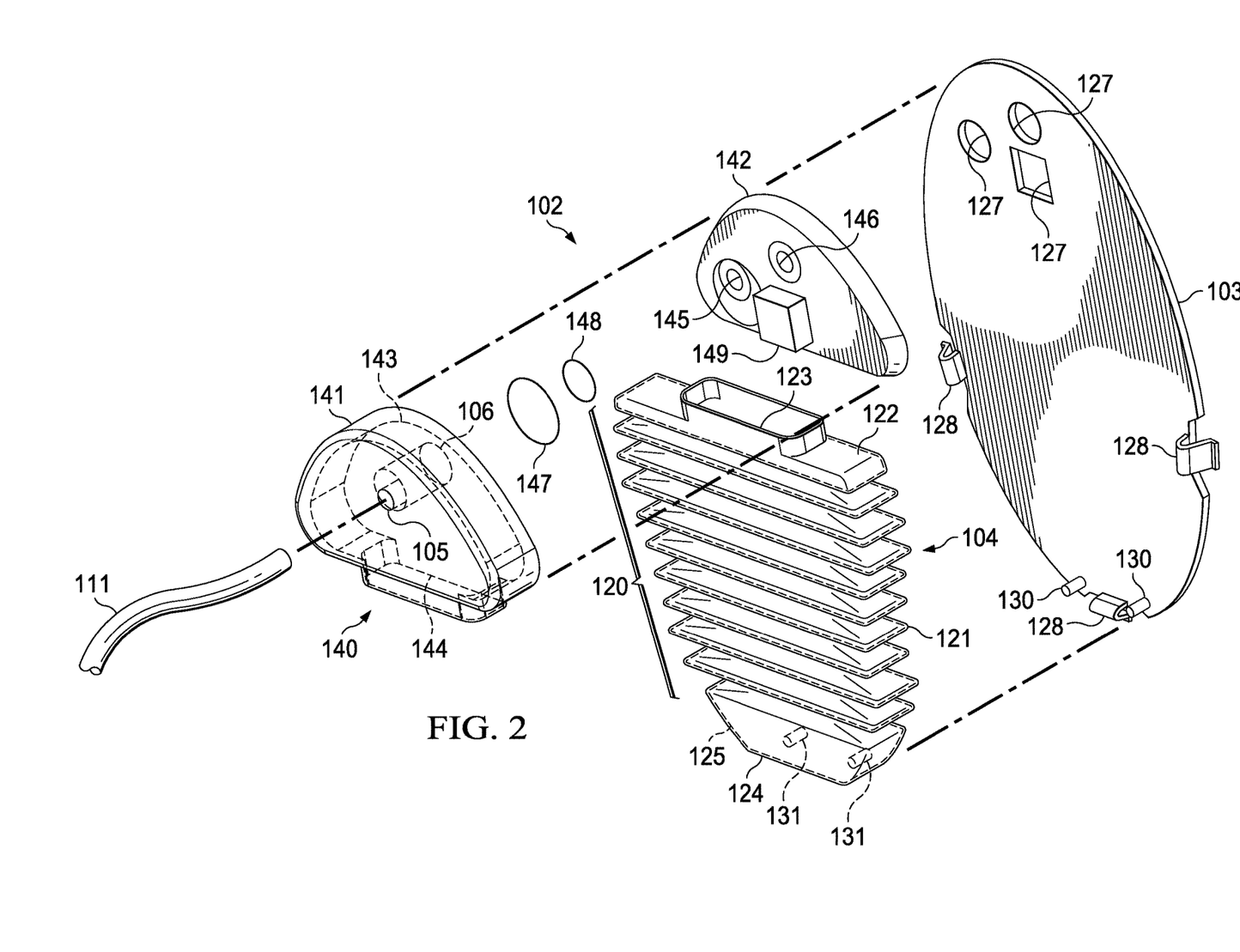
FIG. 2 depicts an exploded view of the fluid collection canister and the supporting member of FIG. 1.
Figure 3:
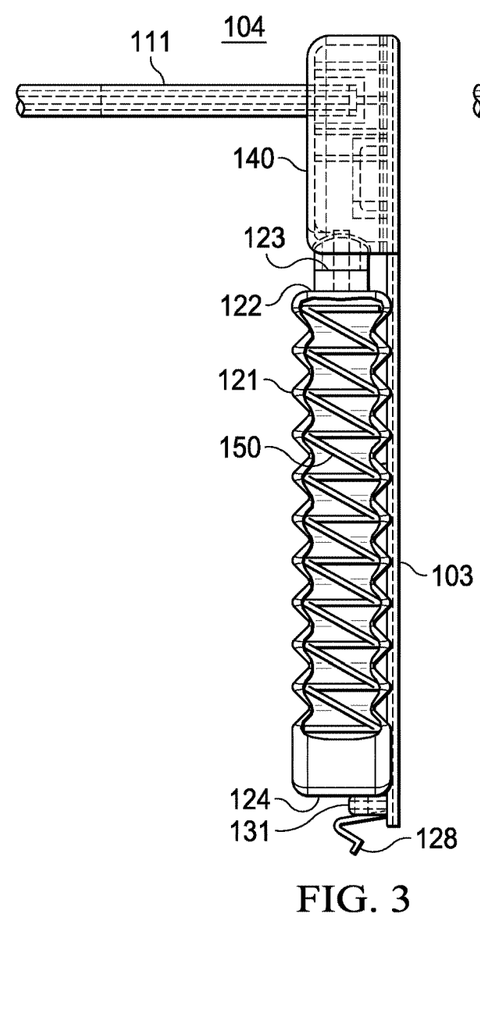
FIG. 3 depicts a sectional, side view of the fluid collection canister containing a coil spring and the supporting member of FIG. 1.

Referring to FIGS. 1, 2 and 3, a reduced pressure treatment system 10 comprises a fluid collection system 100, a reduced pressure treatment unit 101, and a canister 102 fluidly coupled between the fluid collection system 100 and the reduced treatment unit 101 according to one illustrative embodiment. The canister 102 comprises a support member such as, for example, a carrier plate 103 that is releasably connectable to the reduced pressure treatment unit 101, a container 104 supported by the carrier plate 103, and an inlet 105 and an outlet 106. The fluid collection system 100 comprises a wound dressing 110 fluidly coupled to the inlet 105 of the canister 102 via a conduit or tube 111 containing at least one lumen for the transmission of fluids, both gaseous and liquid. The wound dressing 110 is adapted to be positioned proximate a tissue site 112 for distributing reduced pressure to the tissue site 112. The wound dressing 110 may comprise a tube connector 114 adapted to be fluidly coupled to the tube 111, and a distribution manifold 116 fluidly coupled to the tube connector 114.

The wound dressing 110 may further comprise a drape 118 adapted to cover the distribution manifold 116 for providing a substantially airtight seal over the tissue site 112 to maintain the reduced pressure at various desired levels. The drape 118 may include an adhesive seal (not shown) that not only maintains of the reduced pressure at various levels, but also holds the wound dressing 110 in place over the tissue site 112. The distribution manifold 116 may be a bioabsorbable or bioinert material capable of distributing reduced pressure to the tissue site 112. In one embodiment, the distribution manifold 116 may be an open cell, reticulated foam comprising, for example, a polyurethane material. The wound dressing 110 delivers reduced pressure to a tissue site 112 to provide therapeutic treatment to the tissue site 112 and collect exudates and bodily fluids 113 from the tissue site 112.

The reduced pressure treatment unit 101 may comprise a reduced pressure source (not shown) having an inlet port 107 and a processing unit (not shown) for controlling various features of the reduced pressure treatment unit 101. The inlet port 107 of the reduced pressure source may be fluidly coupled to the outlet 106 of the canister 102 for providing reduced pressure to the flexible container 104 of the canister 102. The reduced pressure source may be a reduced pressure or vacuum pump driven by a motor. In another embodiment, the reduced pressure source may be a manually-actuated pump such as a compressible bellows pump. In still another embodiment, the reduced pressure source may be a wall suction port either with or without a separate pressure regulator.

The reduced pressure source and the processing unit may both be housed within the reduced pressure treatment unit 101 which may also contain sensors, processing units, alarm indicators, memory, databases, software, display units, and user interfaces that further facilitate the application of reduced pressure treatment to the tissue site. In one example, a sensor (not shown) may be disposed at or near the reduced pressure source to determine a source pressure generated by the reduced pressure source. The sensor may communicate with the processing unit that monitors and controls the reduced pressure delivered by the reduced pressure source.

In one embodiment, the container 104 comprises walls 120 that form a chamber within the container 104, a proximal end 122 including an opening 123 to the chamber, and a distal end 124 that is closed. The opening 123 may be fluidly coupled to the inlet 105 and the outlet 106 of the canister 102. The walls 120 may have a collapsible portion that allows the container 104 to be compressed to an empty volume and expanded to a filled volume (the filled volume being greater than the empty volume). It is desirable that the walls 120 have a collapsible portion so that containers 104 when empty can be stored and shipped in a collapsed state of the empty volume to reduce the space consumed. When the canister 102 is snapped into place on the reduced pressure treatment unit 101 prior to being used, a caregiver may expand or stretch the walls 120 outwardly from the collapsed state to an expanded state to allow the container 104 to be filled with wound fluids 113 when reduced pressure is applied.

In one embodiment, the collapsible portion of the walls 120 may be corrugated such that the walls 120 are formed from reticulations 121 comprising a series of generally parallel grooves and ridges that fold down on each other in a direction generally perpendicular to the reticulations 121. The walls 120 may also have a non-corrugated or rigid portion adjacent the opening 123 to provide structure for fluidly coupling the opening 123 within the canister 102. The walls 120 may also have a non-corrugated or rigid portion that provides a pocket 125 adjacent the distal end 124 that may contain gelling agents used to solidify the wound fluids 113 contained within the container 104. In another embodiment, the collapsible portion of the walls 120 may be formed from reticulations 121 having gradually increasing or decreasing diameters so that the walls 120 collapse telescopically around each other rather than folding down on top of each other.

The carrier plate 103 of the canister 102 may be, for example, a thermoplastic plate that supports the container 104 and is releasably connectable to the reduced pressure treatment unit 101. The outlet 106 of the canister 102 is fluidly coupled to the inlet port 107 of the reduced pressure treatment unit 101 when the carrier plate 103 is connected to the reduced pressure treatment unit 101. The carrier plate 103 may include a set of apertures 127 at the proximal end of the carrier plate 103 through which the outlet 106 of the canister 102 may be fluidly coupled to the reduced pressure treatment unit 101 including the inlet port 107. The apertures 127 allow the canister 102 to be fluidly coupled to the reduced pressure treatment unit 101 without contaminating the carrier plate 103 with bodily fluids 113 and exudates drawn from the tissue site 112. The carrier plate 103 may be connected to the reduced pressure treatment unit 101 by a plurality of connection devices such as, for example, latches 128 that are formed on the carrier plate 103 such that the latches 128 mate with and eject from the reduced pressure treatment unit 101 by pushing the carrier plate 103 into position on the reduced pressure treatment unit 101 and then releasing the latches 128 to remove the carrier plate 103. Other types of connection systems may be used to hold the carrier plate 103 in position facilitating removal of the carrier plate 103 from the reduced pressure treatment unit 101. In another embodiment, the carrier plate 103 may be affixed to the reduced pressure treatment unit 101.

The carrier plate 103 further comprises a retaining means or a retention device to ensure that the collapsible portion of the walls 120 does not compress or collapse under atmospheric pressure when reduced pressure is applied to the tissue site 112 by the reduced pressure treatment unit 101 and ultimately applied to the chamber of the container 104. In one embodiment, the retention device may be formed at the distal end of the carrier plate 103 for coupling to the distal end 124 of the container 104 when the walls 120 are stretched to the expanded state as described above. The retention device may be, for example, at least one boss having a male boss portion 130 extending from the carrier plate 103 and a female boss portion 131 in the container 104 for receiving the male boss portion 130 which holds the walls 120 of the container 104 in the extended state when reduced pressure is being applied to the tissue site 112 and ultimately to the chamber of the container 104.

In operation, the container 104 is packaged in its collapsed state to reduce the volume of the container 104 when packaged for shipping. When the caregiver opens the package containing the container 104 and connects the opening 123 of the container 104 to the carrier plate 103, the caregiver may then draw the distal end 124 of the container 104 down to the distal end of the carrier plate 103 stretching the walls 120 into the expanded state and may hook the female boss portion 131 of the container 104 to the male boss portion 130 of the carrier plate 103 to hold or retain the container 104 in the expanded state when reduced pressure is being applied to the tissue site 112 and the canister 102. The retention device may be implemented by other embodiments to ensure that the collapsible portion of the walls 120 does not collapse under atmospheric pressure.

In another embodiment, the retention device may include a coiled spring 150 positioned within the chamber of the container 104 as shown in FIG. 3. Initially, the spring may be in a compressed state when being stored or shipped in a package. When the caregiver connects the opening 123 of the container 104 to the carrier plate 103 and then draws the distal end 124 of the container 104 down to the distal end of the carrier plate 103, the coiled spring unravels to the expanded state to further resist compression of the collapsible portion of the walls 120 under atmospheric pressure when reduced pressure is applied.

Figure 4:
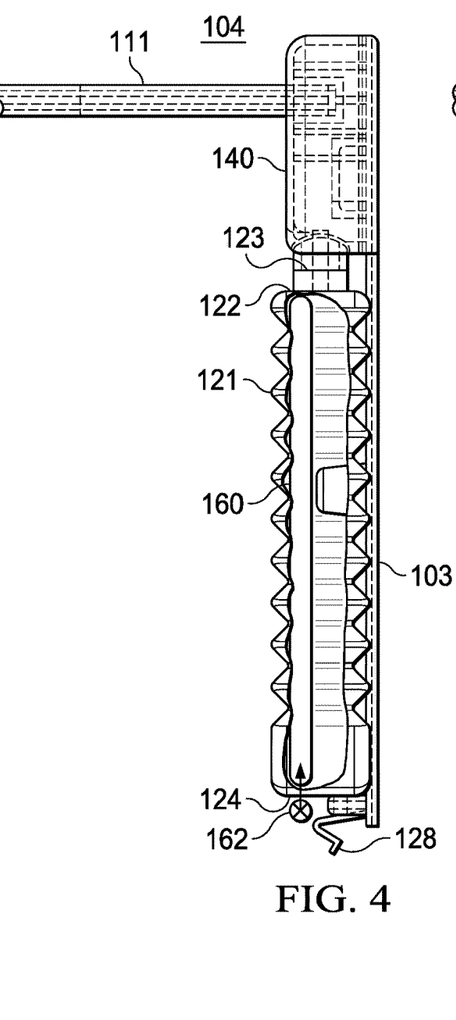
FIGS. 4 and 5 depict a sectional, side view of the fluid collection canister containing a fluidic device the supporting member of FIG. 1.

In yet another embodiment shown in FIG. 4, the retention device may include a pneumatic pouch 160 disposed within the chamber of the container 104 and an intake valve 162 having an orifice extending through the distal end 124 of the container 104 in fluid communication with the pneumatic pouch 160. The pneumatic pouch 160 may be a separate component that is formed from a flexible thermoplastic material that is collapsible within the chamber of the container 104. When the caregiver draws the distal end 124 of the container 104 down to the distal end of the carrier plate 103 to stretch the walls 120 into the expanded state, air is drawn through the intake valve 162 into the pneumatic pouch 160 and cannot be released from the pneumatic pouch 160 until the intake valve 162 is opened. Other gases may also be used to inflate the pneumatic pouch 160 such as, for example, carbon dioxide. Additionally, the pneumatic pouch 160 may be inflated by using a source of positive pressure to inflate the pneumatic pouch 160 through the inlet valve 162. This may be accomplished by using the exhaust from the source of reduced pressure within the reduced pressure treatment unit 101. Thus, when the caregiver charges the pneumatic pouch 160 as described, the pneumatic pouch 160 further resists compression of the collapsible portion of the walls 120 under atmospheric pressure when reduced pressure is applied.

Figure 5:
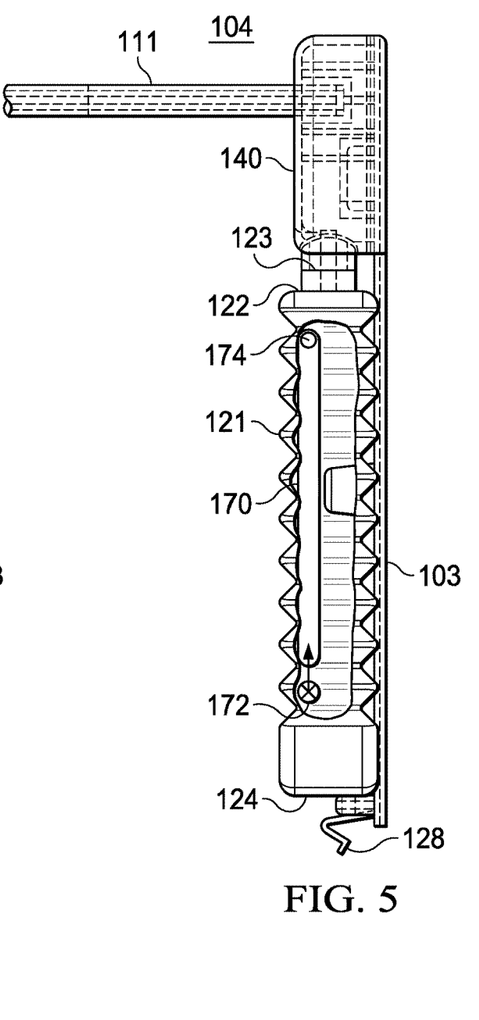

In still another embodiment shown in FIG. 5, the retention device may include a bladder 170 having a distal and a proximal end disposed within the chamber of the container 104, an intake valve 172 disposed in the distal end of the bladder 170, and a hydrophobic filter 174 disposed within an aperture in the proximal end of the bladder 170. Reduced pressure may be used to draw a measured quantity of bodily fluids into the bladder 170 through the intake valve 172 so that the bladder 170 becomes more rigid within the chamber of the container 104. When the bladder 170 is filled such that the bodily fluids reaches the hydrophobic filter 174 which becomes occluded so as to prevent any additional liquid from entering the chamber of the container 104 while providing structural support to the collapsible portion of the walls 120.

In another embodiment, the canister 102 may further comprise a fluid interface member such as, for example, an interface connector 140. Referring more specifically to FIG. 2, the interface connector 140 comprises a container portion 141, and engagement plate 142 closing the container portion 141 to form an interface chamber 143 within the interface connector 140, and a neck opening 144 for receiving the opening 123 of the container 104 and fluidly coupling the interface chamber 143 to the chamber of the container 104. The interface connector 140 may include the inlet 105 and the outlet 106 of the canister 102. The engagement plate 142 may have apertures 145 and 146 for supporting filters 147 and 148, respectively. The filter 147 may be a hydrophobic filter associated with the output 106 of the canister 102. The filter 148 may be a filter associated with the pressure sensor in the reduced pressure treatment unit 101 as described above. The engagement plate 142 may also comprise a latching mechanism 149 that holds the interface connector snugly against the reduced pressure treatment unit 101 to ensure that the outlet 106 of the canister 102 tightly engages the inlet port 107 of the reduced pressure treatment unit 101. The interface connector 140 and the engagement plate 142 may be formed from a rigid plastic and affixed to the carrier plate 103 of the canister 102.

A method for collecting bodily fluids from a tissue site is provided according to an illustrative embodiment. The method includes expanding a canister having a variable volume from a first volume to a second volume, the second volume being greater than the first volume. The method may further comprise affixing the canister to a carrier plate, whereby the volume of the canister is maintained substantially at the second volume. The method may further comprise releasing a retainer on a spring disposed within the canister, whereby the spring maintains the volume of the canister substantially at the second volume. The method may further comprise charging a fluidic device disposed within the canister with a fluid such that the fluidic device becomes substantially rigid and whereby the volume of the canister is maintained substantially at the second volume. The method further includes creating a reduced pressure within the canister to draw bodily fluids from the tissue site to the canister.

It should be apparent from the foregoing that an invention having significant advantages has been provided. While the invention is shown in only a few of its forms, it is not just limited but is susceptible to various changes and modifications without departing from the spirit thereof.

The invention claimed is:

1. A fluid collection canister for collecting bodily fluids from a tissue site by using reduced pressure provided from a reduced pressure treatment unit, comprising:
    a carrier plate having a generally rigid body, a proximal end, a distal end, and an aperture;
    an interface connector coupled to the carrier plate, the interface connector including an interface chamber, an inlet adapted to receive bodily fluids from the tissue site, an outlet adapted to be fluidly coupled to the reduced pressure treatment unit through the aperture for receiving reduced pressure, and a first opening;
    a container having walls forming a chamber within the container, a proximal end including a second opening adapted to be coupled with the first opening to fluidly couple the interface chamber and the chamber of the container, and a distal end closing the chamber, wherein the walls have a collapsible portion allowing the container to be compressed to a first volume in a collapsed state and stretched to a second volume in an expanded state, the second volume being larger than the first volume; and
    a retention device adapted to retain the distal end of the container proximate to the distal end of the carrier plate to hold the container in the expanded state while the reduced pressure from the reduced pressure treatment unit is communicated to the chamber.

2. The canister of claim 1, wherein the retention device is a pneumatic pouch positioned within the chamber of the container.

3. The canister of claim 1, wherein the collapsible portion is corrugated.

4. The canister of claim 1, wherein the walls further comprise a non-collapsible portion.

5. The canister of claim 1, wherein the retention device is a boss.

6. The canister of claim 1, wherein the retention device comprises a coil spring positioned within the chamber of the container.

7. The canister of claim 1, wherein the interface connector comprises a container portion and an engagement plate, the container portion and the engagement plate forming the interface chamber.

8. The canister of claim 7, wherein the interface connector further comprises a canister latching mechanism adapted to hold the interface connector against the reduced pressure treatment unit.

9. The canister of claim 7, wherein the engagement plate further comprises an aperture adapted to support an outlet hydrophobic filter at the outlet of the canister.

10. The canister of claim 1, wherein the walls have a non-corrugated portion providing a pocket adjacent to the distal end of the container, wherein the pocket contains a gelling agent configured to solidify wound fluid received in the container.

11. The canister of claim 1, wherein the carrier plate includes a plurality of latches and wherein the plurality of latches are configured to mate with and eject from the reduced pressure treatment unit.

12. A fluid collection canister for collecting bodily fluids from a tissue site, comprising:
    a carrier plate configured to be releasably coupled to a reduced pressure treatment unit, the carrier plate having a proximal end, a distal end, and a length between the proximal end and the distal end;
    a container having a proximal end, a distal end, and a collapsible portion between the proximal end and the distal end, the container configured to be compressed to a first volume in a collapsed state and stretched to a second volume in an expanded state, the second volume being larger than the first volume, and wherein the distal end of the container is configured to be moved along the length of the carrier plate between the collapsed state and the expanded state; and
    a retention device adapted to retain the distal end of the container proximate to the distal end of the carrier plate.

13. The canister of claim 12, wherein the collapsible portion is corrugated.

14. The canister of claim 12, wherein the container further comprises a non-collapsible portion.

15. The canister of claim 12, wherein the retention device is a boss.

16. The canister of claim 12, wherein the retention device comprises a coil spring positioned within the container.

17. The canister of claim 12, wherein the canister further comprises an interface connector comprising a container portion and an engagement plate, the container portion and the engagement plate forming an interface connector chamber, the interface connector chamber fluidly connected to the container.

18. The canister of claim 17, wherein the interface connector further includes an inlet and an outlet of the canister.

19. A fluid collection canister for collecting bodily fluids from a tissue site, comprising:
    a support member having a proximal end, a distal end, and a length between the proximal end and the distal end;
    an expandable container having a proximal end and a distal end, wherein the distal end of the expandable container is configured to be moved along the length of the support member between a compressed state and an expanded state; and
    a retention device adapted to retain the distal end of the support member at the distal end of the support member.

* * * * *